United States Patent
Kitayama et al.

(10) Patent No.: US 7,030,261 B2
(45) Date of Patent: Apr. 18, 2006

(54) METHOD FOR PREPARING 2-HYDROXY-6-UREIDOCARBONYL NAPHTHALENE DERIVATIVE

(75) Inventors: Masaya Kitayama, Takarazuka (JP); Hiroyuki Wakamori, Hikami-gun (JP); Nobuhiro Yonetani, Nishinomiya (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 11/048,876

(22) Filed: Feb. 3, 2005

(65) Prior Publication Data

US 2005/0192442 A1    Sep. 1, 2005

(30) Foreign Application Priority Data

Feb. 4, 2004    (JP) ............................. 2004-028343

(51) Int. Cl.
*C07C 205/45*    (2006.01)
*C07C 253/30*    (2006.01)
*C07C 275/30*    (2006.01)

(52) U.S. Cl. .......................... 558/415; 560/21; 564/50
(58) Field of Classification Search .................. 560/21; 558/415; 564/50
See application file for complete search history.

(56) References Cited

FOREIGN PATENT DOCUMENTS

EP    0 765 858 A1    4/1997

*Primary Examiner*—Peter O'Sullivan
(74) *Attorney, Agent, or Firm*—Sughrue Mion, PLLC

(57) ABSTRACT

Disclosed is a method for preparing a 2-hydroxy-6-ureidocarbonyl naphthalene derivative. The method comprises the step of reacting 2-hydroxy-6-aminocarbonyl naphthalene and a isocyanate in an organic solvent at a temperature of 90–200° C. According to the present invention, 2-hydroxy-6-ureidocarbonyl naphthalene derivative can easily be obtained within relatively short time and high yield.

4 Claims, No Drawings

METHOD FOR PREPARING 2-HYDROXY-6-UREIDOCARBONYL NAPHTHALENE DERIVATIVE

FILED OF THE INVENTION

The present invention relates to a method for preparing a 2-hydroxy-6-ureidocarbonyl naphthalene derivative.

BACKGROUND OF THE INVENTION

Among condensed aromatic compounds which can provide conjugated polyene system and have absorption in the electron band, 2-naphthol derivatives are relatively inexpensive and are employed widely in the industrial field. For example, 2-naphthol derivatives are used for manufacturing coloring materials such as dyes and pigments, photosensitive materials and polymer materials such as liquid crystalline polymers.

Among various 2-naphthol derivatives, 2-hydroxynaphthoic acid derivatives wherein the carboxylic acid group is converted to aminocarbonyl or ureidocarbonyl group are especially useful as coupler component for manufacturing azo pigments.

For manufacturing amidated 2-hydroxynaphthoic acid derivative, there are several industrially applicable efficient methods; for example, it can be obtained by reacting corresponding acid halogenated compound and an amine. For manufacturing 2-hydroxy-ureidocarbonyl naphthalene derivative, there is a proposed method which contains the step of reacting acid chloride of the 2-hydroxynaphthalene-3,6-dicarboxylic acid and urea derivative to give the 3,6-di-ureidocarbonyl derivative (see U.S. Pat. No. 6,252,104, the contents is herein incorporated by reference). However said method is not suitable for industrial synthesize since it takes quite a long time and provides only a low yield.

SUMMARY OF THE INVENTION

An object of the present invention is to provide a method for manufacturing 2-hydroxy-6-ureidocarbonyl naphthalene derivative which can provide the desired compound within a shorter time with high yield.

The present invention provides a method for preparing a 2-hydroxy-6-ureidocarbonyl naphthalene derivative, which comprises the step of reacting a 2-hydroxy-6-aminocarbonyl naphthalene derivative represented by formula [1]:

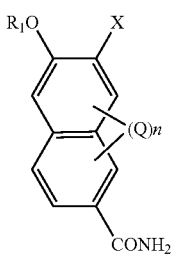

wherein X is hydrogen atom, cyano group or a group represented by formula [2], [3] or [4] below:

 [2]

wherein $X_1$ is selected from the group consisting of an optionally branched and optionally substituted C1–20 aliphatic hydrocarbon group which may have unsaturated bond(s), an optionally substituted aromatic group and an optionally substituted heterocyclic group having conjugated double bonds;

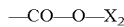 [3]

wherein $X_2$ is an optionally branched C1–6 aliphatic hydrocarbon group which may have unsaturated bond(s);

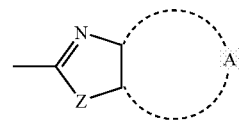 [4]

wherein A is selected from the group consisting of an optionally substituted aromatic group and an optionally substituted heterocyclic group having conjugated double bonds, and Z is selected from the group consisting of —O—, —S— and —NH—;

Q is selected from the group consisting of optionally branched C1–6 alkyl and alkoxy groups, halogen atom, nitro group and nitroso group;

n is an integer of 0–3; and $R_1$ is selected from the group consisting of hydrogen atom, C1–6 alkyl, C2–6 acyl and phenylalkyl groups, with a isocyanate represented by formula [5]:

 [5]

wherein

Y is selected from the group consisting of an optionally substituted aromatic group and an optionally substituted heterocyclic group having conjugated double bonds, in an organic solvent at a temperature of 90–200° C. to give the 2-hydroxy-6-ureidocarbonyl naphthalene derivative represented by formula [6]:

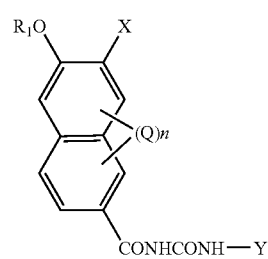

wherein X, Q, n, $R_1$ and Y are the same as defined above.

DETAILED DESCRIPTION OF THE INVENTION

In the present specification and claims, "lower" represents a group having 1–6 carbon atoms.

"Aromatic group" represents a 6-membered monocyclic aromatic group or condensed ring group consisting of up to 4 of 6-membered aromatic rings.

"Heterocyclic group having conjugated double bonds" represents a 5- or 6-membered mono-cyclic group or condensed ring group having at least one hetero-atom selected from N, S and O and conjugated double bonds. When it represents a condensed ring group, said group may have up to 6 rings.

The 2-hydroxy-6-aminocarbonyl naphthalene derivative of formula [1], the starting material in the method of the present invention, as well as 2-hydroxy-6-ureidocarbonyl naphthalene of formula [6], the product, may have a substituent at its 3-position. The substituent may be cyano group, or group represented by formula [2], [3] or [4].

Examples of the groups represented by formula [2] may include alkylaminocarbonyl, naphthylaminocarbonyl and phenylaminocarbonyl groups.

Examples of the optionally substituted aromatic group of $X_1$ of formula [2] may include benzene, naphthalene and anthraquinone rings. Examples of the optionally substituted heterocyclic group having conjugated double bonds of $X_1$ may include thiophene, furan, pyrrole, imidazole, pyrazole, isothiazole, isoxazole, pyridine, pyrazine, pyrimidine, pyridazine, triazole, tetrazole, indole, 1H-indazole, purine, 4H-quinolizine, isoquinoline, quinoline, phthalazine, naphthylidine, quinoxaline, quinazoline, cinnoline, pteridine and benzofuran.

Examples of substituents of those groups may include halogen atom, halogenated lower alkyl, nitro, lower alkyl, lower alkoxy such as methoxy, cyano, phenoxy, pyrimidylamino, benzoylamino, sulfonic, esterified carboxyl such as alkoxycabonyl and phenoxycarbonyl, amidized carboxyl such as phenylaminocarbonyl, alkylaminosulfonyl and alkenyl group of 2–6 carbon atoms which may include aryl group.

When the substituent contains an aromatic ring, the compound may further have one or more substituents such as halogen atom, lower alkyl, lower alkoxy, phenyl and cyano groups-on said aromatic ring.

Examples of the groups represented by formula [3] may include methoxycarbonyl, ethoxycarbonyl, n-propyloxycarbonyl, iso-propyloxycarbonyl and n-butylcarbonyl groups.

Examples of the groups represented by formula [4] may include benzothiazolyl, benzoxazolyl and imidazolyl groups. Examples of the optionally substituted aromatic groups of A in formula [4] may include benzene, naphthalene and anthraquinone rings. Examples of the optionally substituted heterocyclic group having conjugated double bonds of A in formula [4] may include thiophene, furan, pyrrole, imidazole, pyrazole, isothiazole, isoxazole, pyridine, pyrazine., pyrimidine, pyridazine, triazole, tetrazole, indole, 1H-indazole, purine, 4H-quinolizine, isoquinoline, quinoline, phthalazine, naphthylidine, quinoxaline, quinazoline, cinnoline, pteridine and benzofuran.

2-hydroxy-6-aminocarbonyl naphthalene of formula [1] as well as 2-hydroxy-6-ureidocarbonyl naphthalene derivative of formula [6] may have substituent(s) represented by "Q". Examples of the substituents Q may include optionally branched lower alkyl or lower alkoxy groups, halogen atom, nitro and nitroso groups. When the number of the substituents represented by "n" is 2 or 3, the Qs may be the same or different.

$R_1$ in formula [1] as well as formula [6] is selected from the group consisting of hydrogen atom, C1–6 alkyl group, C2–6 acyl group such as acetyl, and phenylalkylene group such as benzyl. Among them, C1–6 alkyl, C2–6 acyl and phenylalkyl groups act as protecting groups for the hydroxy group during the reaction and are preferable to avoid side reaction.

In case 2-hydroxy-6-ureidocarbonyl naphthalene derivative of formula [6] wherein $R_1$ is hydrogen atom is desired, the $R_1$ of the starting material may preferably be those protecting group of C1–6 alkyl, C2–6 acyl or phenylalkyl. Those protecting group may be removed after the reaction to convert the aminocarbonyl group into ureidocarbonyl group is completed. Deprotection of lower alkyl or phenyl alkyl protecting group may be carried out with aluminum chloride or hydrobromic acid. Deprotection of lower acyl protecting group may be carried out with a basic agent such as sodium hydroxide or an acidic agent such as sulfuric acid.

According to the present invention, the 2-hydroxy-6-aminocarbonyl naphthalene derivative of formula [1] wherein $R_1$ is C2–6 acyl group, X is hydrogen atom and n is 0 may preferably be used as starting material because it can easily be synthesized with lower cost.

The 2-hydroxy-6-aminocarbonyl naphthalene derivative of formula [1] may be prepared by any known method, for example, according to scheme 1 shown below. That is, a hydroxynaphthoic acid derivative [7] is treated with thionyl chloride to give an acid chloride derivative [8] and the acid chloride derivative is treated with ammonia to give desired 2-hydroxy-6-aminocarbonyl naphthalene derivative of [1].

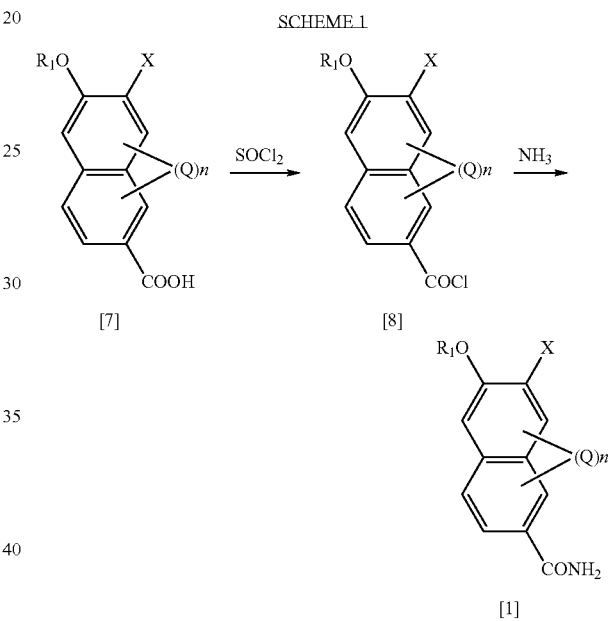

SCHEME 1

In formulae [7] and [8], X, Q, n and $R_1$ are the same as those in the definition of formula [1].

The naphthol derivative of formula [7] wherein X is a group of formula [2], [3] or [4] may be prepared according to the method disclosed in WO96/32366 and WO01/87859, the contents of which are incorporated herein by reference. The compound of formula [7] wherein X is cyano group may be prepared according to scheme 2 shown below:

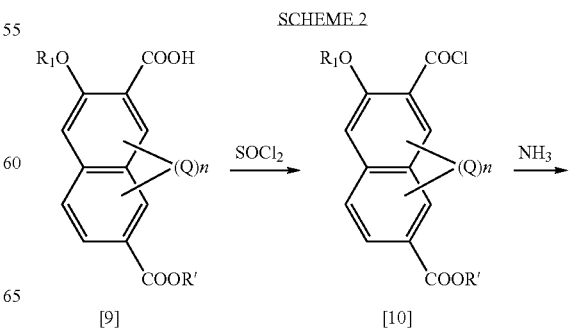

SCHEME 2

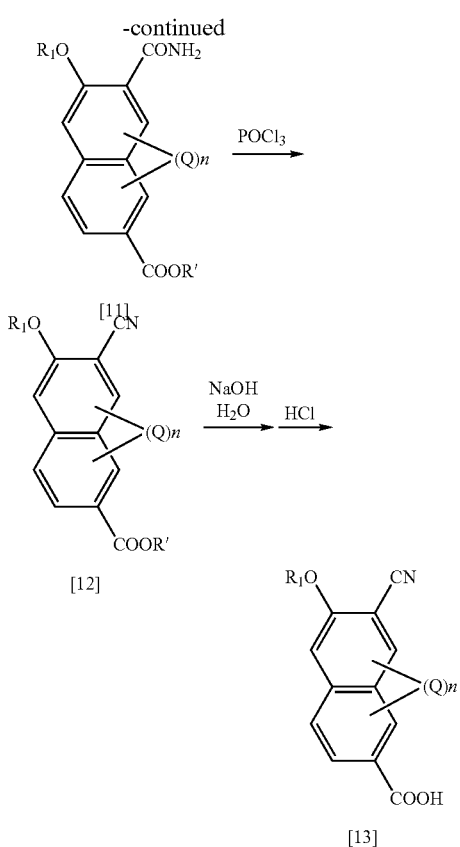

In formulae [9]–[13], Q, n and $R_1$ are the same as those in the definition of formula [1]. R' represents a lower alkyl group.

According to the present invention, isocyanate of formula [5]:

OCN—Y    [5]

wherein Y is an optionally substituted aromatic group or an optionally substituted heterocyclic group having conjugated double bonds is reacted with 2-hydroxy-6-aminocarbonyl naphthalene derivative of formula [1] to give the ureido-derivative.

Examples of the group Y in formula [5] may include phenyl, naphthyl, pyridyl, pyrimidinyl, pyridazinyl, quinolinyl, benzothiazolyl, benzoxazolyl, benzimidazolyl and benzimidazolonyl groups.

Examples of the substituent on Y may include halogen atom, lower alkyl, halogenated lower alkyl, lower alkoxy, optionally substituted phenoxy, nitro, cyano, optionally substituted phenylaminocarbonyl, optionally substituted benzoyl, lower acylamino, optionally substituted benzoylamino and lower alkylamino sulfonyl groups. When said substituent has further substituent, examples of the further substituents may include halogen atom, lower alkyl, halogenated lower alkyl, lower alkoxy, nitro and cyano groups.

The isocyanate derivative of formula [5] may be prepared by treating an amine with a phosgenating agent such as phosgene or triphosgene in a solvent such as ethylacetate at room temperature.

According to the present invention, the reaction between the 2-hydroxy-6-aminocarbonyl naphthalene derivative of formula [1] and the isocyanate of formula [5] is carried out at a temperature of 90–200° C., preferably 100–180° C., more preferably 120–150° C. When the reaction temperature is lower than 90° C., solubility of the naphthol derivative in said solvent becomes very low and the reaction speed is extremely reduced. When the reaction temperature is higher than 200° C., too much energy will be required for heating and undesirable side reaction may occur with some isocyanate.

According to the present invention, the organic solvent used in the reaction is not specifically limited so long as said solvent will not interfere the reaction between isocyanate and the aminocarbonyl group. Preferred organic solvents may include xylene, toluene, mesitylene, nitrobenzene, chlorobenzene, dimethyl sulfoxide, N,N-dimethylformamide, N,N-dimethylacetamide, 1,3-dimethyl-2-imidazolidinone, N-methyl-2-pyrrolidone, hexamethylphosphoramide, sulfolane, tetrahydrofuran, 1,4-dioxane, dichloromethane, ethylene glycol dimethyl ether, diethyl ether and a mixture thereof. Among the above, xylene, toluene, mesitylene, nitrobenzene and chlorobenzene are preferably used as a sole solvent because of their relatively high boiling point.

After the reaction is terminated, the resulting ureido-derivative may be harvested from the reaction mixture in a conventional manner such as concentrating or cooling the mixture to crystallize the product, adding water to the mixture to precipitate the product, or extracting the product from the mixture. If desired, thus obtained product may be purified by recrystallization or washing with an organic solvent or water.

The 2-hydroxy-6-ureidocarbonyl naphthalene derivative obtained by the method of the present invention may be used for manufacturing dyes, pigments such as azo pigments, or liquid crystalline materials. The product is especially useful for manufacturing coloring material, i.e. dyes and pigments since it can facilitate to produce materials having a variety of colors.

EXAMPLES

The present invention is further illustrated by the following examples. Those examples are intended to illustrate the invention and are not to be construed to limit the scope of the invention.

Example 1

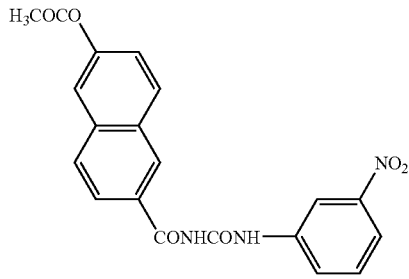

2-acetoxy-6-aminocarbonyl naphthalene 2.3 g (10 mmol) was dispersed in xylene 46 g. 3-nitrophenyl isocyanate 1.97 g (12 mmol, 1.2 fold (mol) of the naphthol derivative) was added thereto. The mixture was reacted at 130° C. for two hours and cooled to room temperature. The precipitates were collected by filtration, washed with methanol, and dried to give 3.2 g of the desired ureido-derivative shown above as white powder. The yield calculated from the starting amount of 2-acetoxy-6-aminocarbonyl naphthalene was 81.4%.

Examples 2–5

Ureido derivatives were prepared in the same manner as Example 1 using 2-hydroxy-aminocarbonyl naphthalene derivatives and isocyanates shown in Table 1.

Results are shown in Table 1.

TABLE 1

| | aminocarbonyl derivative | isocyanate | ureidocarbonyl derivative (product) | yield |
|---|---|---|---|---|
| Ex. 2 | 6-(H₃COCO)-naphthalene-2-CONH₂ | 2-O₂N-C₆H₄-NCO | 6-(H₃COCO)-naphthalene-2-CONHCONH-(2-O₂N-C₆H₄) | 90.8% |
| Ex. 3 | 6-(H₃COCO)-naphthalene-2-CONH₂ | 2,4-Cl₂-C₆H₃-NCO | 6-(H₃COCO)-naphthalene-2-CONHCONH-(2,4-Cl₂-C₆H₃) | 91.5% |
| Ex. 4 | 6-H₃CO-7-CN-naphthalene-2-CONH₂ | 2-Cl-C₆H₄-NCO | 6-H₃CO-7-CN-naphthalene-2-CONHCONH-(2-Cl-C₆H₄) | 74.5% |
| Ex. 5 | 6-HO-7-[CONH-(3-NO₂-C₆H₄)]-naphthalene-2-CONH₂ | 3-NO₂-C₆H₄-NCO | 6-HO-7-[CONH-(3-NO₂-C₆H₄)]-naphthalene-2-CONHCONH-(3-NO₂-C₆H₄) | 72.3% |

Comparative Example 1

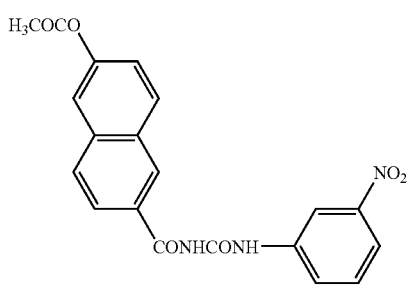

2-acetoxynaphthalene-6-carboxylic acid 9.21 g was dispersed in tetrahydrofuran 73.7 g, N,N-dimethylformamide was added thereto and then, thionylchloride 7.2 g was added thereto. The mixture was reacted for 2 hours at 50° C. After that, unreacted thionylchloride was removed together with the solvent by evaporation. 3-nitrophenyl urea 8.7 g dispersed in tetrahydrofuran 73.7 g was added to the remainder and the mixture was reacted under reflux for more 24 hours. After that, the reaction mixture was cooled to room temperature, the precipitates were collected by filtration. The product was washed with methanol repeatedly to give 2.8 g of the desired compound. The yield calculated from the starting amount of 2-acetoxynaphthalene-6-carboxylic acid was 17.8%.

Examples 6 and 7, Comparative Examples 2 and 3

Reaction of 2-acetoxy-6-aminocarbonyl naphthalene and 3-nitrophenyl isocyanate was carried out in the same manner as Example 1 except for the reaction temperature and the solvent were those shown in Table 2 respectively. After the reaction was completed, the reaction mixture was analyzed with high speed liquid chromatograph and the yield of the desired ureido-derivative was determined. The results are shown in Table 2.

TABLE 2

| | reaction temp. | reaction solvent | yield |
| --- | --- | --- | --- |
| Ex. 1 | 130° C. | xylene | 93.2% |
| Ex. 6 | 100° C. | xylene | 61.3% |
| Ex. 7 | 170° C. | o-dichlorobenzene | 78.3% |
| Com. Ex. 2 | 20° C. | xylene | 0% |
| Com. Ex. 3 | 70° C. | xylene | 2.5% |

What is claimed is:

1. A method for manufacturing a 2-hydroxy-6-ureidocarbonyl naphthalene derivative, which comprises the step of reacting a 2-hydroxy-6-aminocarbonyl naphthalene derivative represented by formula [1]:

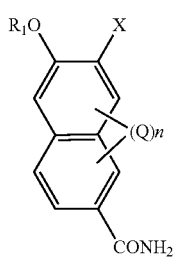

[1]

wherein X is hydrogen atom, cyano group or a group represented by formula [2], [3] or [4] below:

—CONH—X$_1$ [2]

wherein $X_1$ is selected from the group consisting of an optionally branched and optionally substituted C1–20 aliphatic hydrocarbon group which may have unsaturated bond(s), an optionally substituted aromatic group and an optionally substituted heterocyclic group having conjugated double bonds;

—CO—O—X$_2$ [3]

wherein $X_2$ is an optionally branched C1–6 aliphatic hydrocarbon group which may have unsaturated bond(s);

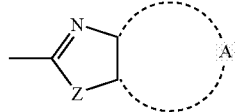

[4]

wherein A is selected from the group consisting of an optionally substituted aromatic group and an optionally substituted heterocyclic group having conjugated double bonds, and Z is selected from the group consisting of —O—, —S— and —NH—;

Q is selected from the group consisting of optionally branched C1–6 alkyl and alkoxy groups, halogen atom, nitro group and nitroso group;

n is an integer of 0–3; and $R_1$ is selected from the group consisting of hydrogen atom, C1–6 alkyl, C2–6 acyl and phenylalkyl groups, with a isocyanate represented by formula [5]:

OCN—Y [5]

wherein Y is selected from the group consisting of an optionally substituted aromatic group and an optionally substituted heterocyclic group having conjugated double bonds, in an organic solvent at a temperature of 90–200° C. to give the 2-hydroxy-6-ureidocarbonyl naphthalene derivative represented by formula [6]:

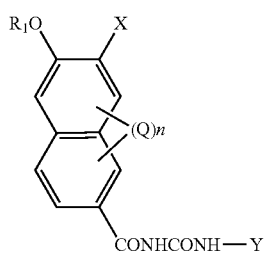

[6]

wherein X, Q, n, $R_1$ and Y are the same as defined above.

2. The method of claim 1, wherein $R_1$ is C2–6 acyl group, X is hydrogen atom and n is 0.

3. The method of claim 1, wherein the organic solvent is selected from the group consisting of toluene, xylene, mesitylene, nitrobenzene and chlorobenzene.

4. The method of claim 2, wherein the organic solvent is selected from the group consisting of toluene, xylene, mesitylene, nitrobenzene and chlorobenzene.

* * * * *